United States Patent [19]
Lipfert et al.

[11] 3,952,737
[45] Apr. 27, 1976

[54] CONTRACEPTIVE

[75] Inventors: Donald E. Lipfert, Woolwich, Maine; Seymour L. Romney; Robert Zeidman, both of Mamaroneck, N.Y.; Willfred Goldschmidt, Greenwich, Conn.

[73] Assignee: The Medevice Company, Greenwich, Conn.

[22] Filed: Aug. 28, 1974

[21] Appl. No.: 501,060

[52] U.S. Cl. .............................................. 128/127
[51] Int. Cl.² .......................................... A61F 5/46
[58] Field of Search ....................................
128/127–131

[56] References Cited
UNITED STATES PATENTS

| 1,083,721 | 1/1914 | Asch | 128/127 |
| 2,145,057 | 1/1939 | Schmid | 128/127 |
| 2,818,856 | 1/1958 | Kohl | 128/127 |
| 2,836,177 | 5/1958 | Sells | 128/127 |

*Primary Examiner*—Lawrence W. Trapp
*Attorney, Agent, or Firm*—Edward Halle

[57] ABSTRACT

A contraceptive device in the form of a pessary or cervical cap for attachment to the cervix, comprising a valve mechanism to permit outflow of material from the cervix and prevent inflow of material into the cervix.

45 Claims, 18 Drawing Figures

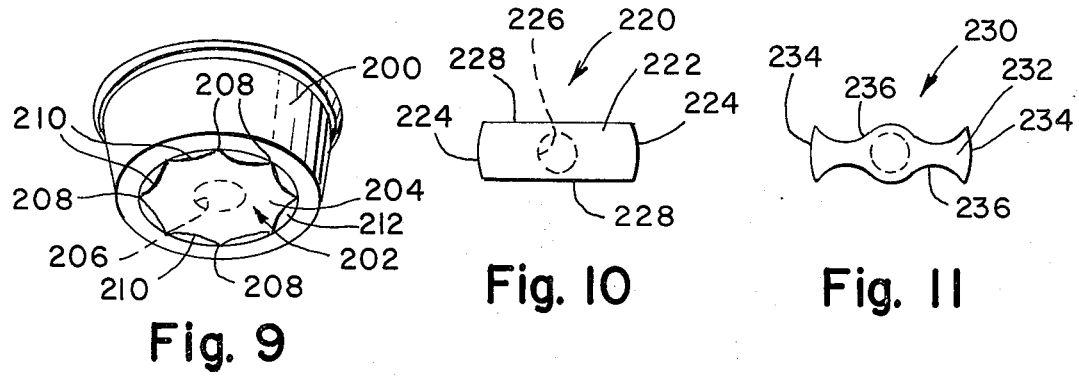
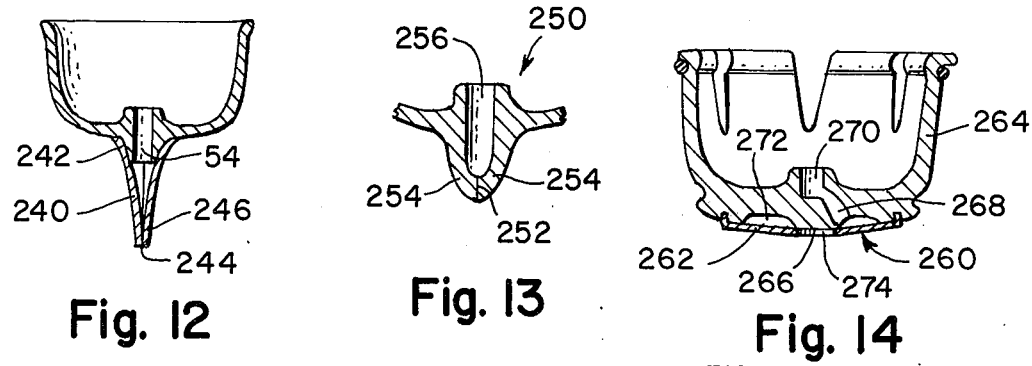
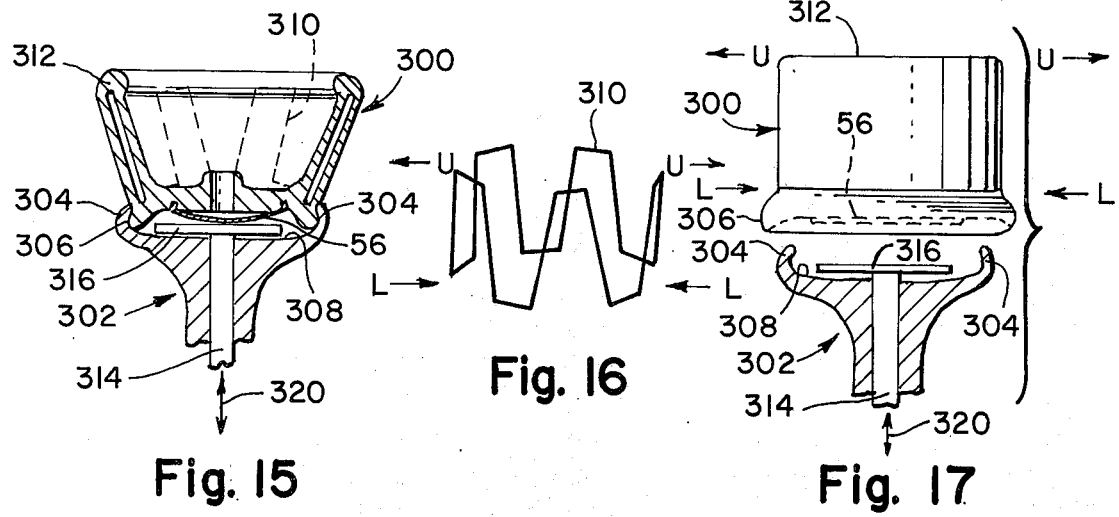

CONTRACEPTIVE

BACKGROUND OF THE INVENTION

Various forms of contraceptive devices of a mechanical nature are known to the art. Some of those are in the form of pessaries or cervical caps designed to cover the opening of the uterus and prevent the inflow of semen. There are also intrauterine devices which require planting intrauterine portions of the device in the sensitive interior of the uterus. Intrauterine devices may also require the use of drugs or medicaments.

The present invention provides a non-intrauterine contraceptive system which will prevent the inflow of sperm to the uterus and yet permit normal menstrual outflow while the device is attached to the uterus without the necessity of using medicaments or drugs in connection therewith.

It is a principal object of the invention to provide a cervical cap which may be applied with little training and may be effectively attached to the cervix for extended periods of time without danger of being rejected or causing side effects from the use of drugs, or from positioning within sensitive portions of the uterus.

BRIEF SUMMARY OF THE INVENTION

The invention is in the form of a cervical cap having provision for clamping or fastening over the cervix. It closes the entrance to the uterus with a valve mechanism that permits outflow of menstrual discharge but seals against inflow of sperm. In the preferred form of the invention the cap has a passageway to permit the outflow of material from the uterus which is closed by a membrane valve. A gate portion of the membrane valve is placed across the passageway to act as a closed gate when pressure is applied from the outside of the cap; however, even a slight pressure generated within the uterus would lift the gate portion of the membrane from the passage opening to permit flow from the passage opening out of the uterus into the vagina. When the device is in position attached to the cervix of the uterus, it will seal the os against the inflow of fluid from the vagina because the membrane gate will always remain closed against the force of pressure from outside the uterus and will prevent flow from the vagina into the uterus. On the other hand, the construction of the device is such that the slightest pressure within the uterus against the membrane valve gate will move the membrane gate portion to permit an outflow. Semen which may be present in the vagina may not enter the uterus, whereas menstrual flow may leave the uterus. A practical result is that the device can be left in position over the uterus for extended periods of time without interference with any of the normal functions of the body. Thus the device can be applied and removed easily and left in position for long periods of time.

The cervix cap of the invention may be provided in its preferred form with a clamping system comprising a cap having a notched cup shaped construction with grooves or flanges to accommodate a selectively movable O ring for sliding between the base of the cup and the lip of the cup. The cup body portion of the cervical cap may be molded from an elastomeric material compatible with the body tissue of the organ about which it is positioned. The sides of the cup diverge somewhat outwardly from the base to the lip so that when the O ring is moved from the base to the lip it will compress the sides of the lip opening around the cervix and seat the elastomeric material of the cup snugly against the organ. Internal projections or beads may be formed inside the cup body portion to aid in making an effective seal clamp around the cervix.

BRIEF DESCRIPTION OF THE DRAWINGS

The invention is illustrated in the drawings in which:

FIG. 9 is a perspective view of another form of the invention having another form of diaphragm valve;

FIG. 10 is a bottom plan view with parts in phantom showing another form of diaphragm valve;

FIG. 11 is a bottom plan view with parts in phantom showing another form of diaphragm valve;

FIG. 12 is a medial cross sectional view showing the invention with an elastomeric tube form of valve;

FIG. 13 is a medial cross section with parts cut away showing a form of the invention with an integrally molded valve;

FIG. 14 is a medial cross section showing a form of the invention with a diaphragm valve having a valve seat construction;

FIG. 15 is an elevational view with part in phantom, part in section and part cut away of another form of invention with applicator attached;

FIG. 16 is a perspective view of a part of the invention shown in FIG. 15; and

FIG. 17 is a view similar to FIG. 15 showing the applicator detached.

Similar numerals refer to similar parts in the views.

DETAILED DESCRIPTION OF THE INVENTION

Figure 1:
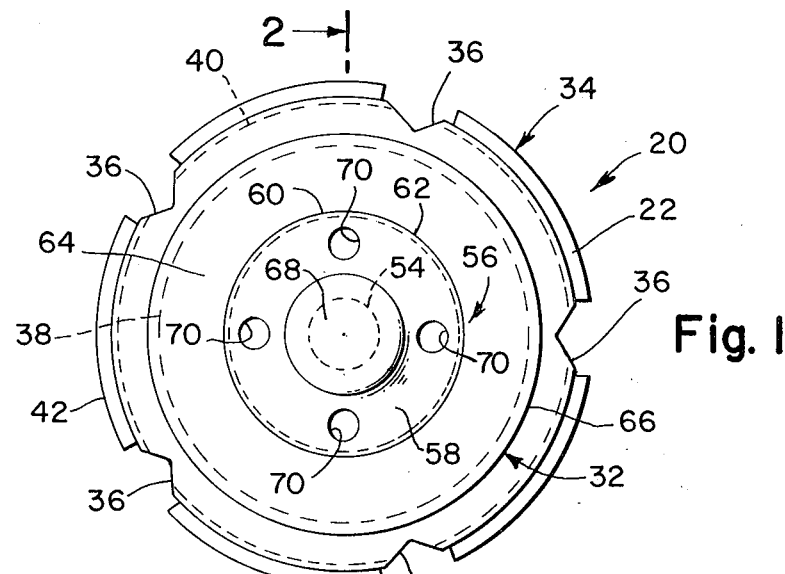
FIG. 1 is a bottom plan view.
Figure 2:
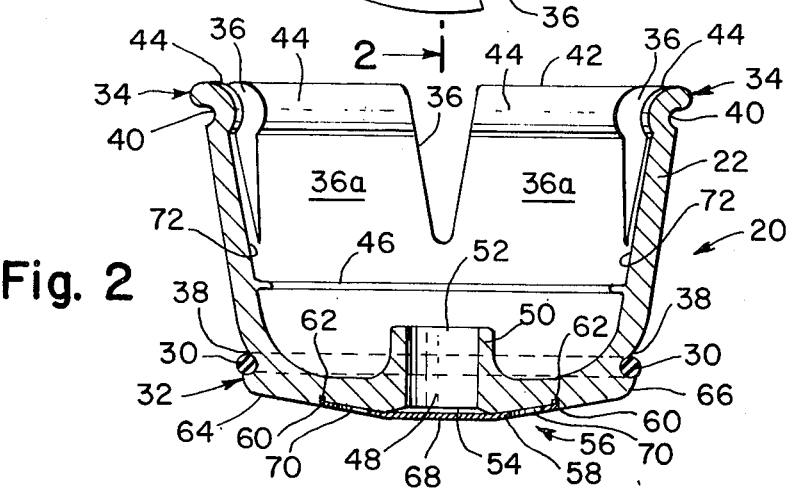
FIG. 2 is a sectional view as seen along the lines 2—2 in FIG. 1.
Figure 3:
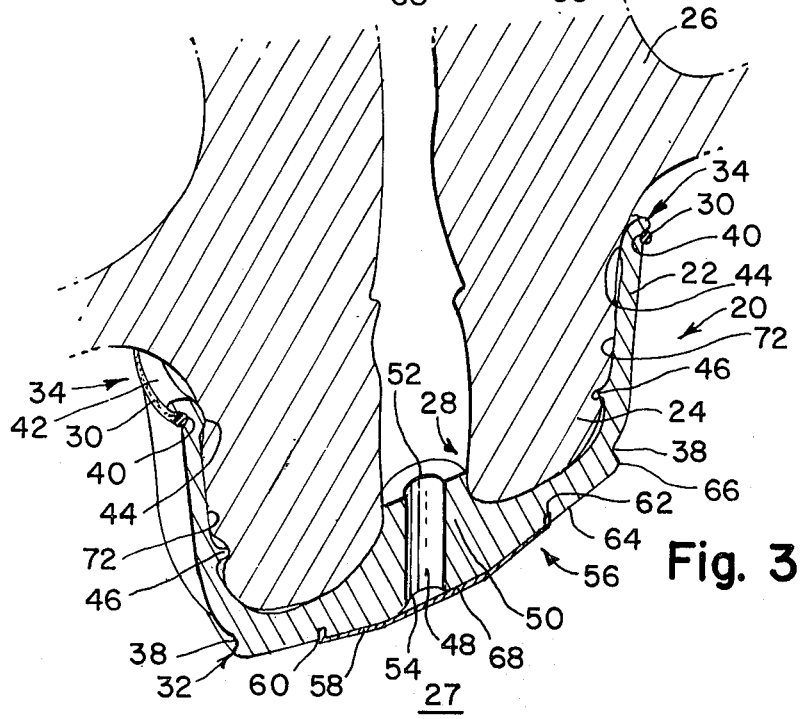
FIG. 3 is a perspective partly broken away and partly in section showing the device in position over the cervix.

The contraceptive device of the invention is preferably in the form of a cervical cap 20 having a cup shaped body portion 22 made of an elastomeric material compatible with the body tissue against which it is to be placed. The cup shaped body portion 22 is designed to fit around the cervix 24 of the uterus 26 and is designed to be clamped or affixed over the cervix 24 to block the os 28, which is the entrance passage to the uterus 26, from flow from the vagina area outside the uterus 26 into the uterus. In the preferred form of invention as shown in FIGS. 1, 2 and 3, the clamping mechanism is provided for principally by means of an O ring 30 which cooperates with the deformable elastomeric material of the body portion 22. Body portion 22 has a base portion 32 and a lip portion 34. In the preferred form the circumference of the lip portion may be somewhat greater than the circumference of the base portion to provide for fitting the cup form of the body 22 over the cervix 24 which can then be deformed toward the cervix 24 by constricting action of the O ring 30 to clamp the body portion 22 against the cervix 24. Notches 36 may be made in the material of the body portion 22 to cooperate in the clamping action. A first O ring positioning means 38 in the form of a groove, as shown in FIGS. 1 through 3, or in the form of a flange or any other such means is provided at the base 32. A second O ring positioning means 40 is provided in the lip portion 34. The O ring 30 may be selectively moved from first position at base portion 32 to second position at lip portion 34 to contract the circumference 42 of the lip portion to clamp around the cervix 24.

The O ring 30 may be made of an elastomeric material. The material of the body portion 22 should be of a type compatible with the organs of the body. A medical grade of silicone as known in the art may be used; however, any material non-reactive with and compatible with intimate contact with living tissue may be used.

The device may be made with a body portion 22 of 2 or 3 (or more) standard sizes to fit women who have had no children and who have already had children. The notches 36 form petals 36a between them which also serve to fit the cup 22 to the cervix 24 which may have a normal range of 2.5 to 3.0 centimeters in diameter.

The clamping function of the device is assisted by an internal bead formation 44 inside of the circumference 42 of the lip portion 34, as well as by an internal bead formation 46 positioned between the notches 36 and the base portion 32. Bead 46 also serves as a sealing ring. The cup shaped body portion 22 is provided with a passageway 48 in the base portion 32. Passageway 48 is contained within a tube-like formation 50 which fits within the entrance to the os 28 to provide a seal between the outside of tube 50 and the inner wall of the os 28. Passageway 48 has an inner opening 52 and an outer opening 54 which is covered by a diaphragm valve mechanism 56. Diaphragm valve mechanism 56 comprises a diaphragm 58, which is a thin membrane made of an elastomeric material such as medical grade silicone, or the like.

The circumference 60 of the membrane 58 is seated in an annular groove 62 disposed around passageway opening 54. The bottom 64 of the cup shaped body portion 22 slopes from the medial portion in which the passageway end 56 is located toward the outer circumference 66. The purpose of this slope, which may be an angle of 15 degrees, is to provide for a taut stretch of the diaphragm 58 over the outer opening 54. Thus, the central portion biasing means designated by reference numeral 68 acts as a closing valve gate to close off exit portion 56. In this valve means construction 56 the gate 68 will effectively seal off any flow from outside the opening 54 into the opening 54.

Valve ports 70 are provided in diaphragm 58 of the valve means 56. When the diaphragm membrane 58 is stretched taut over the bottom 64, the valve port 70 will be closed against the bottom 64 and the membrane gate 68 is taut over opening 54 so that there will be no flow out from the uterus through the passageway 48. However, the slightest pressure from within the uterus will push the gate portion 68 away from opening 54 and permit flow of liquid between the diaphragm 58 and the bottom 64 until the liquid reaches the valve ports 70 at which interval the liquid may flow through the ports 70.

The membrane 58 is bonded by adhesive, or other bonding means, along its circumference 60 to cup bottom 64. It may be heat sealed at the circumference 60 if preferred.

The above described diaphragm valve means 56 therefore provides a one way valve construction which permits flow of liquids from the uterus 26 through the passageway 48 and out of opening 54 through the valve means 56 into the vagina 27 (outside the uterus). The valve means 56 effectively prevents a flow in the reverse direction, thereby preventing semen from entering the uterus from the vagina.

The cervical cap structure of the device is applied to the uterus by placing the cap, with O ring 30 in first position near the base portion 32, over the cervix. The lip portion of the cup of the body portion 22 will be in normally wide position and fit over the cervix. The tube 50 is positioned within the opening of the os 28 and the inside of the bottom of cup 22, as well as the inner portions 72 of the sides of the body portion cup 22, are fitted as snugly as possible against the cervix. O ring 30 is then moved from its first position (groove 38) at the base 32 to its second position (groove 40) at the lip 34; thereby constricting the circumference 42 and tightening the entire body portion cup 22 around the cervix 24 in a clamping condition.

The grip and the seal are assisted by inner bead segments 44 and inner bead sealing ring 46. The device is now in position as shown in FIG. 3 of the drawings and is in operative condition. It may be left in such position during several months or longer and will not interfere with the natural menstrual function because the menstrual flow will be permitted to leave through valve means 56 in the manner described above. The device will prevent sperm from entering the uterus because the valve means 56, as described above, will not permit flow in that direction.

In the preferred form of the invention illustrated in FIGS. 1 through 3 of the drawings, a special applicator may not be required because of the O ring construction. The device is applied by placing it as described and moving the O ring.

Figure 4:
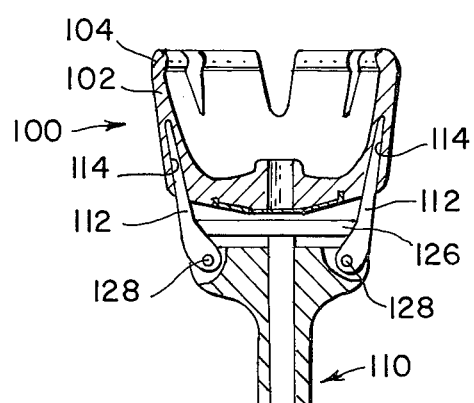
FIG. 4 is an elevational view of another form of the device with parts cut away and parts in section including an applicator for the device.

Anoher form of invention as illustrated in FIG. 4 may be provided where it is desired to have a separate applicator for the device. The contraceptive device 100, as illustrated in FIG. 4, has a cup shaped portion 102 substantially similar to body portion 22 (of FIGS. 1–3) with the exception that the material of the body portion 102 is such that the lip 104, although deformable, is of such strength that it will assume a clamping position around a cervix 24 without the aid of an O ring 30.

In order to apply a device such as device 100 it is therefore necessary to have an applicator which will spread the circumference of the lip portion 104 so that it may fit over the cervix 24 before gripping the cervix in a clamping arrangement. The applicator 110 is provided for this purpose. Applicator 110 has expanding fingers 112 which are adapted to fit into cavities 114 in the walls of the body portion 102. Applicator 110 has manual operating means 116 comprising a hollow handle 118 with a sliding rod 120 and manual gripping portions 122 and 124 attached to hollow handle 118 and central rod 120, respectively. Rod 120 is attached to a piston 126 which when pulled down against the fingers 112 moves them on their hinges 128 to spread them, thereby spreading the walls of the body portion 102 to enlarge the lip circumference 104. This is done by squeezing the grip portions 122 and 124 together to move the central rod 120 and its piston 126 down against the fingers 112. The grip portions 122 and 124 are squeezed to spread the cap 100. When pressure is released on the operating portions 122 and 124 the material of the cap 100 will resume natural unspread condition and grip the uterus 24 firmly. When the applicator is in relaxed position, that is with the fingers not under pressure from the wedge 126, the fingers 112 may be inserted or removed from the cavities 114, as when the cap 100 has been placed in position over the cervix 24.

Figure 5:
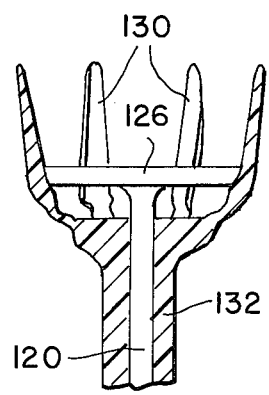
FIG. 5 is an elevational view partly in section with parts cut away showing an alternate form of applicator for the device of FIG. 4.

In FIG. 5 of the drawings an alternate form of applicator is shown in which the fingers 130 are integrally molded to the handle 132 of a material which can be deformed to operate without hinges, such as hinges 128.

Figure 6:
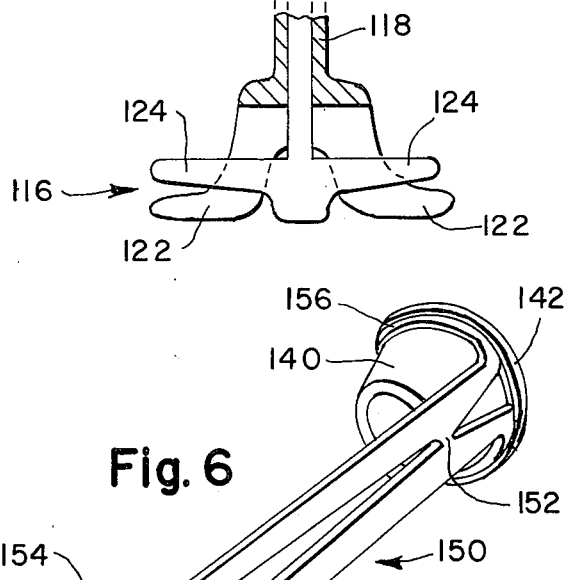
FIG. 6 is a perspective view of another form of the device.
Figure 6A:
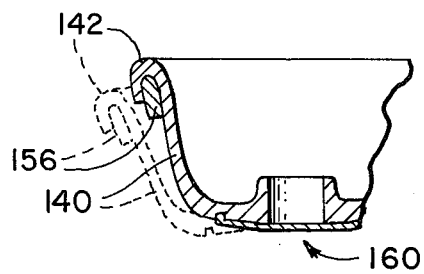
FIG. 6a is a sectional detail of FIG. 6.

In FIGS. 6 and 6a of the drawings another form of invention provided with an applicator is shown. In this form the cup body portion of the device 140 is again made of a material which will grip and clamp the uterus in its normal condition. The material of cup like portion 140 may be spread to apply in the same manner as cup 100, shown in FIG. 4, and for such purpose is provided with an annular rim 142. Annular rim 142 is inturned to form a U-shaped circumference which will fit around the circular end of tool 150. Tool 150 has a scissor-like shape and can be formed with an integral hinge 152 and finger operating portions 154. Tool 150 is provided with an expander ring end 156 adapted to fit in the U-shape of rim 142 around the lip of cup 140. When finger portions 154 are squeezed together, ring 156 is expanded thereby expanding the circumference of the lip of cup 140. Cup 140 is in all other respects similar in the operation of its valve mechanism 160, to valve mechanism 56 of cap 20.

Figure 7:
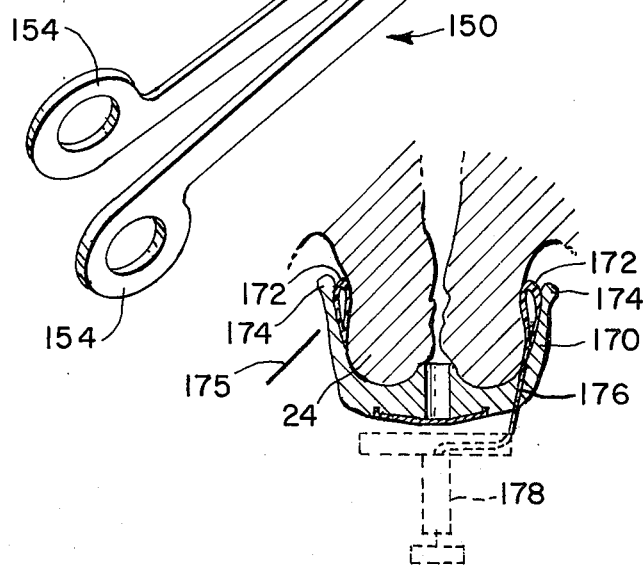
FIG. 7 is a medial cross section of another form of the invention.

Another form of invention is shown in FIG. 7 in which the body portion cup 170 is substantially similar to the body portion cup 22 of the preferred form of the invention and operates in the same manner except for the method of clamping to the cervix 24. Cup 170 has a tubular bladder 172 positioned inside the circumference of lip 174. Tubular bladder 172 is filled with a sealed-in liquid having a vapor pressure that would be low at room temperature but would, at blood temperature, develop sufficient pressure to inflate bladder 172 and secure cup 170 to a cervix 24. The cup 170 could be removed by puncturing the bladder 172 with a needle prick 175 as indicated in FIG. 7 or other means.

In this form of invention the inflating pressure might also be applied by pumping a gas through an applicator from an external source after the cup 170 is in place and then sealed off by removal of the applicator. In such case, an applicator such as any of those described herein would be provided with a hollow puncturing needle 176 leading to a hypodermic syringe 178. These elements are shown in dotted line in FIG. 7, it being understood that they can be incorporated in an applicator of the types described. For example, needle 176 may be incorporated in a finger 114 (FIG. 4) or 130 (FIG. 5) or with ring 156 (FIG. 6). The material of the device adjacent the bladder 172 can be of a self sealing type which closes itself when the needle 176 is removed. Such materials are well known in closures for doseage bottles used with hypodermic syringes.

Figure 8:
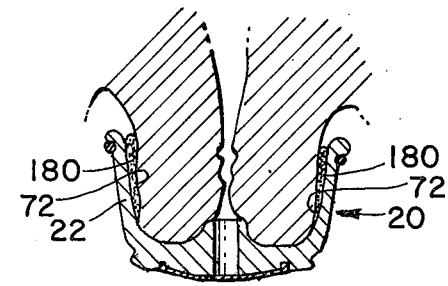
FIG. 8 is a medial cross section of a form of the invention having an auxiliary sealant to conform to irregularities of the cervix.

In FIG. 8 a cervical cap such as cap 20 with body portion 22 is shown in outline. A sealant 180 has been applied to the inside 72 of cup 22 so as to aid the cup 22 to conform to irregularities of the outer surface of the cervix and help to secure the cup 22 in place. Material such as silicone adhesive that would cure in place or denture type adhesives which would remain plastic are among the materials which may be used for the sealant 180.

In FIG. 9 a cup 200 is shown in which the body portion comprises a valve means 202 comprising a diaphragm 204 which is anchored at a plurality of points around the opening 206. Diaphragm 204 does not have valve ports such as valve ports 70, but it does have unbonded areas between the anchoring points 208. Unbonded areas 210 will stretch away from the bottom 212 of the cup 200 if an internal pressure to the opening 206 is placed on the diaphragm and in all other respects the valve means 202 will work in a manner similar to valve means 56.

Another form of valve means 220 is shown in FIG. 10. In this case the strip 222 illustrated in FIG. 10 replaces the diaphragm, such as diaphragm 58 or diaphragm 204. The ends 224 of the strip are bonded to the bottom of a cup, such as cup 22 or one of the other cups described hereinabove, to seal the exit area designated by reference numeral 226 as a dotted circle. Inflow will be sealed by the strip 222. Outflow will be permitted through the unbonded sides 228 of the strip 222.

In FIG. 11 another form of strip valve means 230 is shown in which the strip 232 takes a sort of butterfly shape in which the ends 234 are heat sealed or bonded to the bottom of a cup, such as cup 22, and the curved sides 236 open under pressure to permit outflow of liquid. The shape of this type of valve means 230 reduces tension necessary to work the valve.

Another form of valve which may be used with a cap such as cap 20 having a body portion 22 is shown in FIG. 12. In this figure the exit 54 is covered by a collapsed elastomeric tube valve 240. The inner end 242 of valve 240 is spread around and bonded around opening 54. The outer end of tube valve 240 has a slit 244 and outer end 246. Flow is permitted through slit 244 from opening 54, but pressure from the outside of end 246 keeps slit 244 normally closed and prevents back flow.

A similar slit type valve is shown in FIG. 13. However, instead of being an elastomeric tube valve such as valve 240, it is actually a slit valve 250 which is molded directly into the exit portion 256. A slit 252 is placed between two curved sections 254 of resilient material. This type of slit valve operates in the same manner as the elastomeric tube valve shown in FIG. 12.

In FIG. 14 a type of diaphragm membrane valve 260 is shown in which the diaphragm 262 is positioned at the bottom of cup 264 in the same manner as diaphragm 58 is positioned at the bottom of cup 22. However, in the form shown in FIG. 14, the diaphragm is seated against a valve seat 266 which is centrally located and the exit 268 for the passageway 270 is offset from the center communicating with an annular recess 272 positioned around the valve seat. The valve port 274 is located centrally in the diaphragm 262 and is seated against the valve seat gate 266 to seal the valve from flow from outside the cup 264. Regular menstrual flow can flow out of the cup through the valve arrangement by pressure against the diaphragm which lifts it away from the valve seat 266 to permit outflow through the valve port 274 which sits against the valve seat gate 266 until there is an inside pressure against the diaphragm 262, to open the valve. This has the advantage of having a larger area exposed to the pressure differential actuating forces which close or open the valve.

In FIGS. 15, 16 and 17 another form of invention is shown comprising a cup body portion 300 and applicator 302. Applicator 302 has a fixed gripping rim 304 and the cup body portion 300 has a flexible bead portion 306 around its bottom. The flexible bead portion 306 forms a circumference somewhat larger than the circumference of the fixed rim 304 of the applicator 302 and must be squeezed manually or by other means to diminish its size to squeeze fit it within the rigid rim portion 304 of shallow cup 308 formed at the top of applicator 302, as shown in FIG. 15 of the drawings.

A springy inner frame 310, as shown in FIG. 16, is imbedded within the cup body portion 300. Inner frame 310 has the same shape as the cup body portion 300 when in its normal unsqueezed condition, as shown in FIG. 17, and is embedded within the material of cup body portion 300 by molding the material around it or any other means known to the art.

Reference is now made to FIGS. 16 and 17 of the drawings. In each of the said figures there are a pair of lower arrows L and a pair of upper arrows U. Since the material of cup body portion 300 and the springy frame 310 are resilient or deformable, the pressure against the bottom of cup body portion 300 at the rim 306 in the direction of arrows L will squeeze the bottom of cup body portion 300 inwardly abd compress it to fit within the shallow cup 308. At the same time as the bottom portion at rim 306 is being squeezed inwardly, the upper portion at the upper rim 312 is being squeezed outwardly in the direction of arrows U thereby increasing the diameter of the upper rim 312 so that it may be wider than the intended cervix 24 about which it is to be placed. In this spread condition rim 312 can be easily slipped over the cervix 24.

Applicator 302 has a central piston rod 314 which is manually operated in direction of the double headed arrow 320 by handle or other means similar to that shown in FIG. 4 at reference numerals 122 and 124. Reference is again made to FIG. 15 of the drawings which shows a body portion 300 with bottom rim 306 compressed inwardly and upper rim 312 spread outwardly for insertion. The body portion 300 is inserted over the cervix. Piston rod 314 is then moved upwardly to push piston 316 upwardly against the bottom of body portion 300. This will cause the body portion 300 to be snapped out of the shallow cup 308, permitting removal of applicator and at the same time resulting in contraction of the upper rim 312 and expansion of the lower rim 306 causing the cup 300 to grip itself around the cervix.

In this form of invention the cup 300 may have any of the mechanisms for the valve of the invention as have been described hereinabove. In the form shown in FIGS. 15 through 17 the valve provided is similar to the valve shown and describwd in the form of invention shown in FIG. 2. It is however necessary in the form of invention shown in FIGS. 15, 16 and 17 to provide that the valve means 56 has a bottom which is recessed within the lowest portion of the rim 306 in order for piston 316 to be operative. Thus in using any of the other forms of invention shown hereinabove in conjunction with applicator 302, it is necessary that rim 306 be the lowest portion of the cup body portion 300, as shown in FIG. 15 of the drawings.

While we have described our invention in its preferred forms, there are other forms which it may take without departing from the spirit and scope of the invention and we desire to be protected for all forms coming within the scope of the claims below.

Wherefore we claim:

1. A contraceptive device for positioning in relation to the cervix of the uterus, comprising a body portion, means for holding said body portion to the cervix, and closure means to close the entrance of the cervix from the inflow of material; said closure means comprising valve means comprising at least one opening in said body portion, stretchable diaphragm means including valve gate means and port means, biasing means for biasing said diaphragm means against said body portion with said diaphragm valve gate means against said body portion opening and with said diaphragm port means in offset relationship to said body portion opening; wherein said valve means open upon the application of internal pressure from within the uterus and close upon application of external pressure from without the uterus, to permit the outflow of material under pressure from the uterus and prevent the inflow of material into the uterus.

2. The contraceptive device as claimed in claim 1, in which at least a portion of the valve means is located at a base portion of the body portion.

3. The contraceptive device as claimed in claim 1, in which the diaphragm has a perimeter comprising a plurality of sides with at least one side being attached to the body portion.

4. The contraceptive device as claimed in claim 3, in which the diaphragm comprises a plurality of sides which are attached to the body portion and a plurality of sides free from attachment to the body portion.

5. The contraceptive device as claimed in claim 1, in which the diaphragm is substantially circular and at least one portion of its circumference is attached to the body portion.

6. The contraceptive device as claimed in claim 5, in which the diaphragm is in the form of an elastomeric membrane with its circumference attached to the bottom of the base portion in which the opening is centrally located and the membrane comprises a centrally located valve gate portion in normally faced contacting relation to the base portion opening.

7. The contraceptive device as claimed in claim 6 comprising at least one exit port in the membrane offset from the base portion opening.

8. The contraceptive device as claimed in claim 7, in which the base portion bottom comprises an upward slope between the opening and the membrane circumference.

9. The contraceptive device as claimed in claim 1, in which the biasing means comprises a sloped portion in the body portion.

10. The contraceptive device as claimed in claim 9, in which the diaphragm means is positioned with its valve gate means in contacting relationship against the body portion opening and with said diaphragm port means in contacting relationship against at least a portion of the sloped portion of the body portion.

11. The contraceptive device as claimed in claim 10, in which the opening in the body portion is a centrally located port and the diaphragm has at least one port opening offset from the port opening of the body portion.

12. The contraceptive device as claimed in claim 11, in which at least one offset port opening in the diaphragm overlies the sloped portion of the base.

13. The contraceptive device as claimed in claim 1, in which the bottom of the base portion has a recessed portion communicating with an exit opening from said body portion, a seat portion offset from and below the exit opening and said diaphragm including at least one port overlying the seat portion.

14. The contraceptive device as claimed in claim 1, in which the means for holding the body portion to the cervix comprises a movable O-ring.

15. The contraceptive device as claimed in claim 14, in which the movable O-ring is made of a flexible material.

16. A contraceptive device for positioning in relation to the cervix of the uterus, comprising a cup-like body portion in the form of a cervical cap, an open top adapted to coact with the cervix, a body portion lip portion and a body portion base portion and a first O-ring positioning means between the lip and the base portions, and closure means to close the entrance of the cervix from the inflow of material; said closure means comprising valve means which open upon the application of internal pressure from within the uterus and close upon application of external pressure from without the uterus, to permit the outflow of material under pressure from the uterus and prevent the inflow of material into the uterus; and means for holding the body portion to the cervix comprising a flexible, movable O-ring.

17. The contraceptive device as claimed in claim 16, in which the lip portion is at the open top and second O-ring positioning means is positioned at the lip portion.

18. The contraceptive device as claimed in claim 17, in which the O-ring positioning means comprise groove means to accommodate the O-ring, said O-ring being selectively movable between the first mentioned O-ring positioning groove means and the second mentioned lip positioned O-ring groove means.

19. The contraceptive device as claimed in claim 18, in which the first mentioned groove means is at the base of the cup-like body portion.

20. The contraceptive device as claimed in claim 19, in which the cup-like body portion is made of an elastomeric material.

21. The contraceptive device as claimed in claim 20, in which the cup-like body portion comprises a side wall slanting upwardly and outwardly from the bottom to the lip.

22. The contraceptive device as claimed in claim 21, in which the upper portion of the side wall comprises at least one cut through the lip portion and the first mentioned O-ring groove portion.

23. The contraceptive device as claimed in claim 22, in which there is at least one inner bead in the cup-like body portion between the lip portion and the bottom thereof.

24. The contraceptive device as claimed in claim 23, in which a tube-like passageway extends upwardly from the bottom of the cup-like portion and includes an upper opening for communication with the os and a lower opening comprising an exit opening for cooperation with the diaphragm of the valve means.

25. The contraceptive device as claimed in claim 8 comprising a plurality of notch means at the open top of the cup-like body portion.

26. The contraceptive device as claimed in claim 1, in the form of a cervical cap comprising a cup-like body portion comprising an open top adapted to coact with the cervix and a central inner tube-like passageway for engagement with the os of the cervix.

27. A contraceptive device as claimed in clain 1, comprising a cup-like flexible body portion comprising an open top adapted to coact with the cervix in combination with applicator means.

28. The combination as claimed in claim 27, in which the cup-like body portion has a U-turned lip which cooperates with applicator tool means having an expanding ring to spread the open top of the body portion.

29. A contraceptive device for positioning in relation to the cervix of the uterus, comprising a body portion, means for holding said body portion to the cervix, and closure means to close the entrance of the cervix from the inflow of material; said closure means comprising valve means which open upon the application of internal pressure from within the uterus and close upon the application of external pressure from without the uterus, to permit the outflow of material under pressure from the uterus and prevent the inflow of material into the uterus; said body portion comprising a cup-like flexible body comprising an open top adapted to coact with the cervix in combination with applicator means, in which the cup-like body portion and the applicator means comprise finger-like means on one cooperating with cavities on the other together with means for operating the finger means.

30. The combination as claimed in claim 29 further comprising push-out means.

31. The combination as claimed in claim 29, in which the finger-like means are on the applicator and the cavities are associated with the wall means of the cup body portion, and said finger-like means are operable laterally to spread the open top of the cup.

32. The contraceptive device as claimed in claim 1, comprising a cup-like flexible body portion comprising an open top adapted to coact with the cervix in which the means for holding the body portion to the cervix comprises at least one bladder formed within the wall means of the cup-like body portion containing a fluid pressure exerting body.

33. The contraceptive device as claimed in claim 32, in which the fluid pressure exerting body is a gas having a low vapor pressure at room temperature and a higher vapor pressure at blood temperature to inflate the bladder containing flexible wall of the cup-like body portion against the cervix.

34. The contraceptive device as claimed in claim 33, in combination with an applicator means comprising a hypodermic needle for selective insertion through self sealing wall material.

35. The combination as claimed in claim 34, which includes an applicator having an elongated body portion and at least one finger-like means comprising the hypodermic needle connected to a hypodermic syringe included in the applicator means.

36. A contraceptive device for positioning in relation to the cervix of the uterus, comprising a body portion, means for holding said body portion to the cervix, and closure means to close the entrance of the cervix from the inflow of material; said closure means comprising valve means which open upon the application of internal pressure from within the uterus and close upon application of external pressure from without the uterus, to permit the outflow of material under pressure from the uterus and prevent the inflow of material into the uterus; said body portion comprising a cup-like flexible body comprising an open top adapted to coact with the cervix in which the means for holding the body portion to the cervix comprises at least one bladder formed within the wall means of the cup-like body portion containing a pressure exerting body, and in which the wall means at the bladder comprises a self sealing material.

37. The contraceptive device as claimed in claim 1, A contraceptive device for positioning in relation to the cervix of the uterus, comprising a body portion, means for holding said body portion to the cervix, and closure means to close the entrance of the cervix from the inflow of material; said closure means comprising valve means which open upon the application of internal pressure from within the uterus and close upon application of external pressure from without the uterus, to permit the outflow of material under pressure from the uterus and prevent the inflow of material into the uterus; said body portion comprising a cup-like flexible body comprising an open top adapted to coact with the cervix in which the means for holding the body portion to the cervix comprises adhesive means placed within at least one portion of the inside of the cup-like flexible body portion.

38. A contraceptive device for positioning in relation to the cervix of the uterus, comprising a body portion, means for holding said body portion to the cervix, and closure means to close the entrance of the cervix from the inflow of material; said closure means comprising valve means which open upon the application of internal pressure from within the uterus and close upon application of external pressure from without the uterus, to permit the outflow of material under pressure from the uterus and prevent the inflow of material into the uterus; said body portion comprising a flexible cup-like body in the form of a cervical cap comprising an open top adapted to coact with the cervix and comprising a circumferential body portion wall between an upper lip and a bottom base of the body portion and an annular bead portion around the bottom portion for cooperating with applicator means; in combination with seperable applicator means comprising a fixed rim and push-out means wherein the outside diameter of the annular bead of the cup-like body portion is greater than the inside diameter of the rim portion of the applicator.

39. The combination as claimed in claim 38 comprising a springy frame associated with the circumferential body portion wall.

40. A contraceptive device for positioning in relation to the cervix of the uterus, comprising a body portion, means for holding said body portion to the cervix, and closure means to close the entrance of the cervix from the inflow of material; said closure means comprising valve means which open upon the application of internal pressure from within the uterus and close upon application of external pressure from without the uterus, to permit the outflow of material under pressure from the uterus and prevent the inflow of material into the uterus; said body portion comprising a flexible cup-like body in the form of a cervical cap comprising an open top adapted to coact with the cervix and comprising a circumferential body portion wall between an upper lip and a bottom base of the body portion, springy inner frame means comprising a plurality of frame members within said circumferential body portion connected in alternate arrangement at their upper and lower ends to form a substantially continuous springy inner frame whereby when said cup-like body is squeezed at the bottom it will compress inwardly while the upper open portion of said cup-like body will expand outwardly thereby increasing the size of the open top greater than its normal size and when the squeeze is released at said annular of the cup-like body the open top will contract toward its smaller normal size.

41. The contraceptive device as claimed in claim 40 which includes an amnnular bead portion around the bottom portion of the flexible cup-like body.

42. Applicator means for the contraceptive device as claimed in claim 41 comprising a fixed rim and push-out means wherein the inside diameter of the rim portion of the applicator is less than the outside diameter of the annular bead of the cup-like body portion of the device.

43. The contraceptive device as claimed in claim 1, in which the body portion comprises a circumferential wall comprising a springy frame associated with said circumferential body portion wall.

44. The contraceptive device as claimed in claim 43 further comprising an annular bead portion around a bottom portion of the circumferential body portion wall.

45. The contraceptive device as claimed in claim 44, in combination with separable applicator means comprising a fixed rim and push-out means wherein the inside diameter of the rim portion of the applicator is less than the outside diameter of the annular bead of the cup-like body portion.

* * * * *